(12) United States Patent
Crone et al.

(10) Patent No.: US 9,445,740 B1
(45) Date of Patent: Sep. 20, 2016

(54) PATIENT SIGNAL SENSING DEVICE

(71) Applicant: West Affum Holdings Corp., Grand Cayman (KY)

(72) Inventors: William Edward Crone, Fall City, WA (US); Kenneth Frederick Cowan, Kirkland, WA (US); Douglas Keith Medema, Everett, WA (US); Dallas Eugene Meeker, Kirkland, WA (US)

(73) Assignee: WEST AFFUM HOLDINGS CORP., Grand Cayman (KY)

( * ) Notice: Subject to any disclaimer, the term of this patent is extended or adjusted under 35 U.S.C. 154(b) by 222 days.

(21) Appl. No.: 14/319,721

(22) Filed: Jun. 30, 2014

Related U.S. Application Data (60) Provisional application No. 61/841,213, filed on Jun. 28, 2013, provisional application No. 61/841,215, filed on Jun. 28, 2013.

(51) Int. Cl.
*A61B 5/0408* (2006.01)
*A61B 5/0478* (2006.01)
*A61B 5/0492* (2006.01)
*A61B 5/053* (2006.01)
*A61B 5/00* (2006.01)
*A61B 5/04* (2006.01)
*A61B 5/0402* (2006.01)
*A61B 5/0476* (2006.01)
*A61B 5/08* (2006.01)
*A61B 5/11* (2006.01)

(52) U.S. Cl.
CPC ............ *A61B 5/053* (2013.01); *A61B 5/04001* (2013.01); *A61B 5/0402* (2013.01); *A61B 5/0476* (2013.01); *A61B 5/0478* (2013.01); *A61B 5/04085* (2013.01); *A61B 5/0492* (2013.01); *A61B 5/0531* (2013.01); *A61B 5/0816* (2013.01); *A61B 5/11* (2013.01); *A61B 5/6802* (2013.01); *A61B 5/742* (2013.01)

(58) Field of Classification Search
CPC ............ A61B 5/04085; A61B 5/0478; A61B 5/0492; A61B 5/053; A61B 5/0531
USPC ......................................... 600/372, 391–393
See application file for complete search history.

(56) References Cited

U.S. PATENT DOCUMENTS

| | | | | |
|---|---|---|---|---|
| 3,744,482 A | * | 7/1973 | Kaufman ........... | A61B 5/04284 600/372 |
| 3,868,947 A | * | 3/1975 | Holsinger .......... | A61B 5/04004 600/382 |
| 4,448,199 A | * | 5/1984 | Schmid .............. | A61B 5/02438 600/393 |
| 4,539,995 A | * | 9/1985 | Segawa ............... | A61B 5/0408 174/36 |
| 4,602,639 A | * | 7/1986 | Hoogendoorn .... | A61B 5/04004 600/372 |

(Continued)

*Primary Examiner* — Lee S Cohen
(74) *Attorney, Agent, or Firm* — Kavounas Patent Law Office, PLLC (57) ABSTRACT

A device configured to detect a physiological signal of a patient includes a monitor portion and one or more electrode portions. At least one of the electrode portions is made as a non-contact electrode or a dry electrode, with further adjustments according to embodiments. The electrode portion includes a substrate that has a back side and a front side that is configured to be brought proximately to the patient. At the front side, a sensing electrode may detect a patient signal, and a guard electrode may protect this detection by having a suitable shape, such as a ring. At the back side, a circuit may generate an output signal from the detected signal, and couple it to an output conductor. Moreover, the adjustments may include that the circuit can couple a version of the output signal to the guard electrode.

20 Claims, 5 Drawing Sheets

*ELECTRODE PORTION*

(56) References Cited

U.S. PATENT DOCUMENTS

| | | | |
|---|---|---|---|
| 4,763,660 A * | 8/1988 | Kroll | A61B 5/04085 439/77 |
| 5,511,553 A * | 4/1996 | Segalowitz | A61B 5/0006 128/903 |
| 6,148,233 A | 11/2000 | Owen et al. | |
| 6,418,342 B1 | 7/2002 | Owen et al. | |
| 6,643,541 B2 * | 11/2003 | Mok | A61B 5/0002 128/903 |
| 6,865,409 B2 * | 3/2005 | Getsla | A61N 1/0452 128/902 |
| 8,615,283 B2 | 12/2013 | Besio | |
| 8,750,974 B2 | 6/2014 | Baker et al. | |
| 2005/0277822 A1 * | 12/2005 | Manabe | A61B 5/0492 600/393 |
| 2006/0074411 A1 | 4/2006 | Carmel et al. | |
| 2009/0247858 A1 * | 10/2009 | Getsla | A61B 5/411 600/372 |
| 2011/0166434 A1 * | 7/2011 | Gargiulo | A61B 5/04004 600/372 |
| 2014/0100466 A1 | 4/2014 | Hayashi et al. | |
| 2014/0128765 A1 * | 5/2014 | Chetelat | A61B 5/0531 600/547 |

\* cited by examiner

FIG. 1

FIG. 2   *ELECTRODE PORTION*

FIG. 3A   *ELECTRODE PORTION*

ELECTRODE PORTION

PATIENT SIGNAL SENSING DEVICE

CROSS REFERENCE TO RELATED PATENT APPLICATIONS

This patent application claims priority from U.S. Provisional Patent Application Ser. No. 61/841,213, filed on Jun. 28, 2013, the disclosure of which is hereby incorporated by reference for all purposes.

This patent application claims priority from U.S. Provisional Patent Application Ser. No. 61/841,215, filed on Jun. 28, 2013, the disclosure of which is hereby incorporated by reference for all purposes.

BACKGROUND

Electrical signals of a patient have a great diagnostic value as to the state of the patient. Accordingly, some devices detect and measure such signals, for example by using electrodes.

This detecting and measuring is challenging for a number of reasons. First, these electrical signals are very small in the first place, and are further vulnerable to interference by other ambient signals that include radio frequency signals, triboelectric interference, artifacts from torso movement, and so on. The interference is manifested as electrical noise that becomes superimposed on the signal, which prevents accurate detection and measurement.

Second, the electrode's electrical contact with the patient's skin is not ideal, and can present high electrical resistance and/or impedance. This problem has been solved in some instances by applying a gel between the skin and the electrode. The gel contains an electrolyte that facilitates conduction and reduces impedance.

Although the gel solution works well in emergency situations, it is a problem in situations where the electrodes are going to be worn for a long time. Examples include wearable defibrillators, devices worn on the wrist, chest, neck, head, and so on.

BRIEF SUMMARY

The present description gives instances of devices, the use of which may help overcome problems and limitations of the prior art.

In one embodiment, a device is configured to detect a physiological signal of a patient. The device includes a monitor portion and one or more electrode portions. At least one of the electrode portions is made as a non-contact electrode, with further adjustments according to embodiments. Such an electrode portion includes a substrate that has a back side and a front side that is configured to be brought proximately to the patient. At the front side, a sensing electrode may detect a patient signal, and a guard electrode may protect this detection by having a suitable shape, such as a ring. At the back side, a circuit may generate an output signal from the detected signal, and couple it to an output conductor. Moreover, the adjustments may include that the circuit can couple a version of the output signal to the guard electrode.

An advantage over the prior art is that certain types of electrical interference and noise can be prevented while achieving a good common mode rejection ratio, for example in embodiments where the signals from the electrode portions are applied to an instrumentation amplifier. Accordingly, detection and measurement of patient electrical signals can be improved. These electrical signals can be used to ultimately monitor one or more of important bodily functions, such as the patient's ECG, impedance, EEG, respiration, motion, and neurological variations.

These and other features and advantages of this description will become more readily apparent from the Detailed Description, which proceeds with reference to the associated drawings in which:

DETAILED DESCRIPTION

As has been mentioned, the present description is about devices that can detect physiological signals of a patient. Embodiments are now described in more detail.

Figure 1:
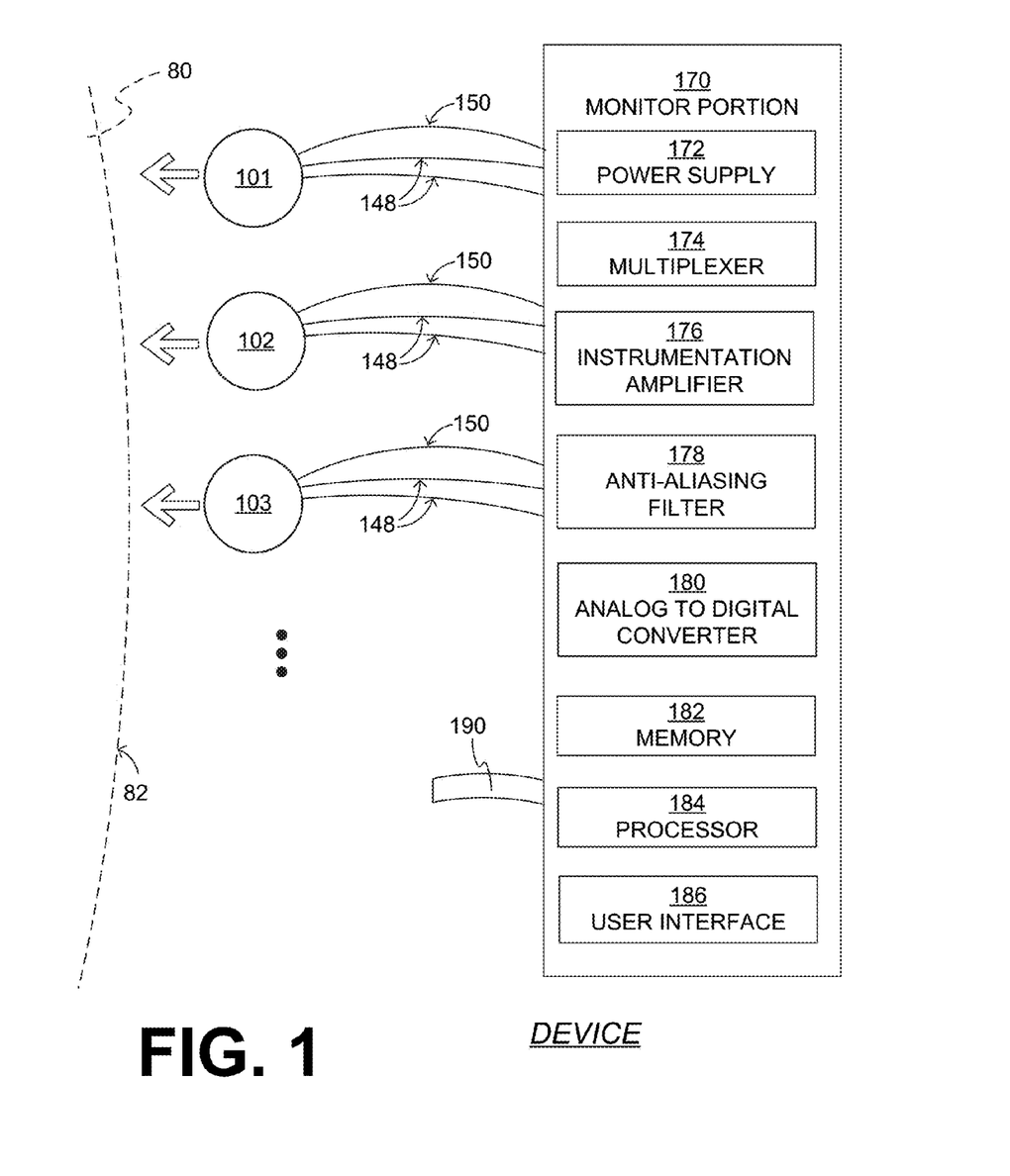
FIG. 1 is a block diagram of a device made according to embodiments.

FIG. 1 is a block diagram of a device 100 made according to embodiments. Device 100 is configured to detect a physiological signal of a patient, such as a patient 80 who has skin 82. Device 100 can be a stand-alone device or a device of any system that detects physiological signals of patient 80. As such, device 100 can be a monitor for a heart related device such as a defibrillator, a wearable defibrillator, a wearable ECG monitor, a device that is used by those who exercise, and so on.

Device 100 includes a monitor portion 170 and one or more electrode portions 101, 102, 103, . . . , at least one of which is made according to embodiments. In this example three electrode portions are shown, but a different number is possible, e.g. two through 13, or even more. Electrode portions 101, 102, 103, . . . are configured to be brought proximately to patient 80 as seen by the arrows, so as to detect respective patient signals.

In the shown embodiment, each of the electrode portions 101, 102, 103 is connected to monitor portion 170 via an output conductor 150 and two power wires 148. Depending on the application, these wires can be embedded in a support structure that the patient wears, which is described below. In other embodiments, such as a wrist-worn device, the output conductor and power wires are internal, all within a casing and inaccessible to a person such as patient 80 or a bystander.

Monitor portion 170 includes a power supply 172 that can include a battery, a rechargeable battery, a transformer configured to transform power from a power outlet, in an isolated form, and so on. Power supply 172 can be configured to provide power via power wires 148 to circuits of electrode portions 101, 102, 103. These circuits generate output signals from the detected patient signals, and transmit the output signals back to monitor portion 170 via their respective output conductors 150.

In other embodiments, a power supply might instead be provided on the electrode portions. In fact, the latter may communicate with a monitor portion wirelessly.

In the shown embodiment, monitor portion 170 includes also a multiplexer 174. Multiplexer 174 receives output signals from output conductors 150, and selects only one of them at a time for further processing, then another, and so on until it rotates through the available signals. In embodiments, this further processing is performed by an instrumentation amplifier 176, an anti-aliasing filter 178, and an analog to digital converter 180. Each of electrode portions 101, 102, 103, . . . operates as an individual lead, and measurements can be taken as differences between the outputs of the individual leads. Analog to digital converter 180 is configured to render a digital value for the output signal that has been carried by the output conductor, after it has been so processed.

In the shown embodiment, monitor portion 170 additionally includes a memory 182 that can be configured to store the digital value, a processor 184 for control and other operations, and a user interface 186. User interface 186 can be controlled by processor 184, can output human perceptible indications of the status of device 100 and of the digital values, can receive inputs by an operator for being controlled, and so on. Accordingly, user interface 186 can be embodied with a screen, a touchscreen, one or more lights, a speaker, controls, and so on. In addition, monitor portion 170 can include a communication device for wired or wireless communication of signals that encode the status of device 100 and the digital values.

In the shown embodiment, monitor portion 170 moreover includes a support structure 190, which is shown only iconically. Support structure 190 can be configured to attach at least a portion of device 100, such as monitor portion 170, to patient 80. As such, support structure can be a vest, a harness, a belt, a garment, a wrist band, a band applied around the leg, and the like. Support structure 190 is thus useful when device 100 is a wearable device.

Electrode portions 101, 102, 103, . . . are now described in more detail. These can be made from a non-contact electrode, which may include polymers, rubber, silver fabric, other conductive fabric, conductive fillers or coatings, etc. A non-contact electrode does not necessarily make contact with human tissue, and can be brought close to it by being pressed against a thin garment. A non-contact electrode is defined as an electrode that has no DC current, and its DC impedance is theoretically infinite. It should be noted that embodiments of these electrode portions 101, 102, 103, . . . may also work with a dry, or a wet electrolyte.

Figure 2:
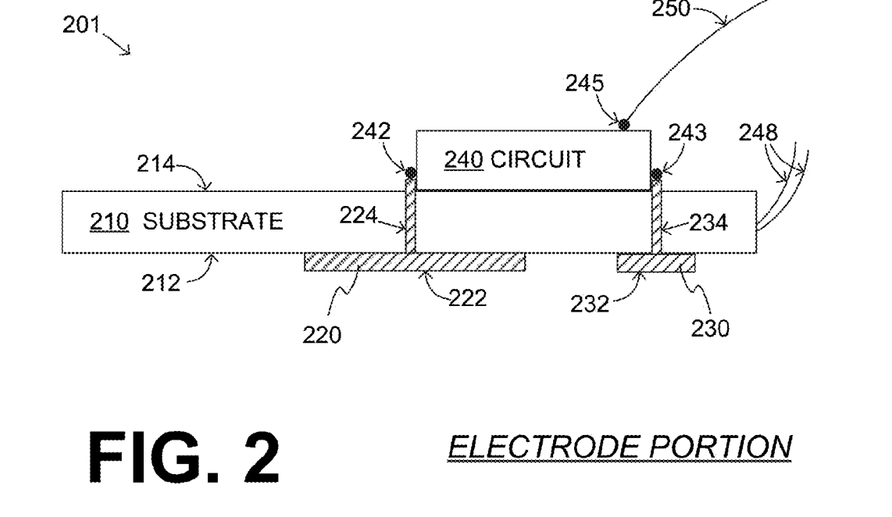
FIG. 2 is a side view of an electrode portion that could be any one of electrode portions of the device of FIG. 1, made according to embodiments.

FIG. 2 is a side view of an electrode portion 201, made according to sample embodiments. Electrode portion 201 could be any one or more of electrode portions 101, 102, 103, . . . of device 100 of FIG. 1.

Electrode portion 201 includes a substrate 210. In FIG. 2, substrate 210 is shown as a rectangle of a certain width and a certain height that corresponds to thickness, but that is done only for illustrating features. In actual embodiments the aspect ratio can be very different than that implied by FIG. 2, with the width relatively much larger and the height/thickness relatively much smaller.

Substrate 210 has a front side 212 and a back side 214. Front side 212 can be configured to be brought proximately to the patient, when the whole electrode portion 201 is brought proximately to the patient as described above. Front side 212 can be brought to have direct physical contact with the patient's skin, or just be close to it. At least front side 212 is non-conductive; in some embodiments, the entire substrate 210 is non-conductive.

Substrate 210 can be hard or flexible. In some embodiments, substrate 210 is configured to be fixedly attached to the patient's skin, such as by adhesive. In such embodiments, the flexibility can help substrate 210 conform to any wrinkles in skin 82. Other means of making the entire structure conformal to the tissue can include non-adhesive methods where the surface tension is sufficient to hold the assembly in place.

Electrode portion 201 additionally includes a conductive sensing electrode 220. Sensing electrode 220 is made conductive by including conductive materials such as metal or other conductive material that is capable of interfacing with other electronics.

Sensing electrode 220 has a plate 222 that is maintained at front side 212 of substrate 210. It is maintained there by being attached to it, coupled to it, or having a shape that suitably interacts with the shape of substrate 210. Plate 222 is configured to detect a patient signal, when front side 212 is brought proximately to the patient. Plate 222 can be made from conductive cloth or wire mesh or a polymer with conductive fillers or the like so as to be flexible, for example in embodiments where substrate 210 is also flexible.

Sensing electrode 220 also has a sensing stub 224 that extends from plate 222 through substrate 210 to back side 214. Sensing stub 224 may extend through a hole of substrate 210, thus permitting the patient signal detected by plate 222 to be transported to back side 214. As mentioned above, in some embodiments the thickness of substrate 210 is very small and thus stub 224 can be correspondingly very short. For consistency in description across drawings, stub 224 is shown as terminating at a node 242, which will be described later from its electrical viewpoint of delivering the transported detected signal. Moreover, embodiments where plate 222 is maintained at front side 212 without being attached to it can be implemented, for example, by having a portion of stub 224 that supports node 242 be actually physically larger than the hole that stub 224 goes through; the whose sensing electrode 320 may be thus retained by not being able to get out of that hole in either direction.

Electrode portion 201 moreover includes a conductive guard electrode 230. As will be seen later, guard electrode 230 may help shield plate 222 of sensing electrode 220 from receiving other ambient signals. As such, guard electrode 230 may prevent interference in the detection of the patient signals by sensing electrode 220. Prevention may be accomplished according to embodiments by further adjusting the shape of guard electrode 230 as will be described later. Embodiments further prevent interference by suitably electrically biasing guard electrode 230, as is now described.

In particular, guard electrode 230 has a section 232 that can be maintained at front side 212 of substrate 210. Section 232 can be electrically insulated from plate 222 as measured on front side 212 of substrate 210, although there can be electrical connections in other places, such as back side 214. Advantageously, section 232 and plate 222 can have low profiles.

Guard electrode 230 also has a guard stub 234 that extends from section 232 through substrate 210 to back side 214. A person skilled in the art will determine that many aspects in the construction of guard electrode 230 can be advantageously similar to parallel aspects of sensing electrode 220. Moreover, guard stub 234 can be considered to terminate at an electrical node 243 on back side 214. As such, a signal that is applied to electrical node 243 will be also applied to section 232, which may improve the prevention of interference.

Electrode portion 201 furthermore includes a circuit 240. Circuit 240 can be attached to back side 214 of substrate 210. Circuit 240 can be coupled to input the detected signal from sensing stub 224, e.g. from electrical node 242. For operations of circuit 240, electrical power can be received, for example from power wires 248 similar to power wires 148 described in FIG. 1. In FIG. 2 the complete connection of power wires 248 to circuit 240 is not shown so as to not clutter the drawing.

Circuit 240 can be further configured to generate an output signal from the input detected signal, as will be described in more detail later. The output signal can be representative of the input signal, and with improved electrical properties for easier downstream processing.

Electrode portion 201 also includes an output conductor 250 similar to output conductors 150 described in FIG. 1. Output conductor 250 can be coupled to receive the output signal from circuit 240, for example at an electrical node 245. Once receiving it, output conductor 250 can thus transport the output signal to a monitoring portion such as monitoring portion 170 of FIG. 1. When considered together with other similar output conductors, any one of them can be called first, second, and so on. Output conductor 250 can be made in any way known in the art, preferably with further provisions for shielding. For example, output conductor 250 can be the center conductor of a cylindrical coaxial cable or equivalent.

According to embodiments, with appropriate electrical connections, circuit 240 can be further configured to couple a version of the output signal to guard stub 234, for example at electrical node 243. This way the version of the output signal will be also applied to section 232, which may improve the prevention of interference. In some embodiments this version of the output signal is the output signal itself, in which case electrical node 243 coincides with electrical node 245. In other embodiments, this version of the output signal can be generated by passing the output signal through electrical components, and so on.

Figure 3A:
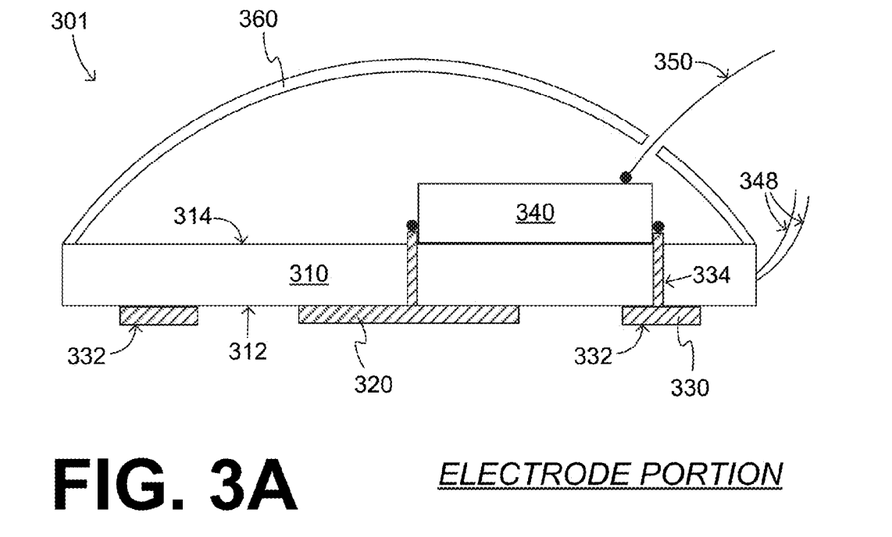
FIG. 3A is a side view of an electrode portion that could be any one of electrode portions of the device of FIG. 1, made according to other embodiments.

Additional embodiments are now described. FIG. 3A is a side view of an electrode portion 301, which could be any one or more of the electrode portions of the device of FIG. 1.

Electrode portion 301 includes a substrate 310 having a front side 312 and a back side 314. It also includes a sensing electrode 320, a circuit 340, power wires 348, and an output conductor 350. It will be recognized that many of these features are similar to corresponding features of FIG. 2, except adapted for the differences.

Figure 3B:
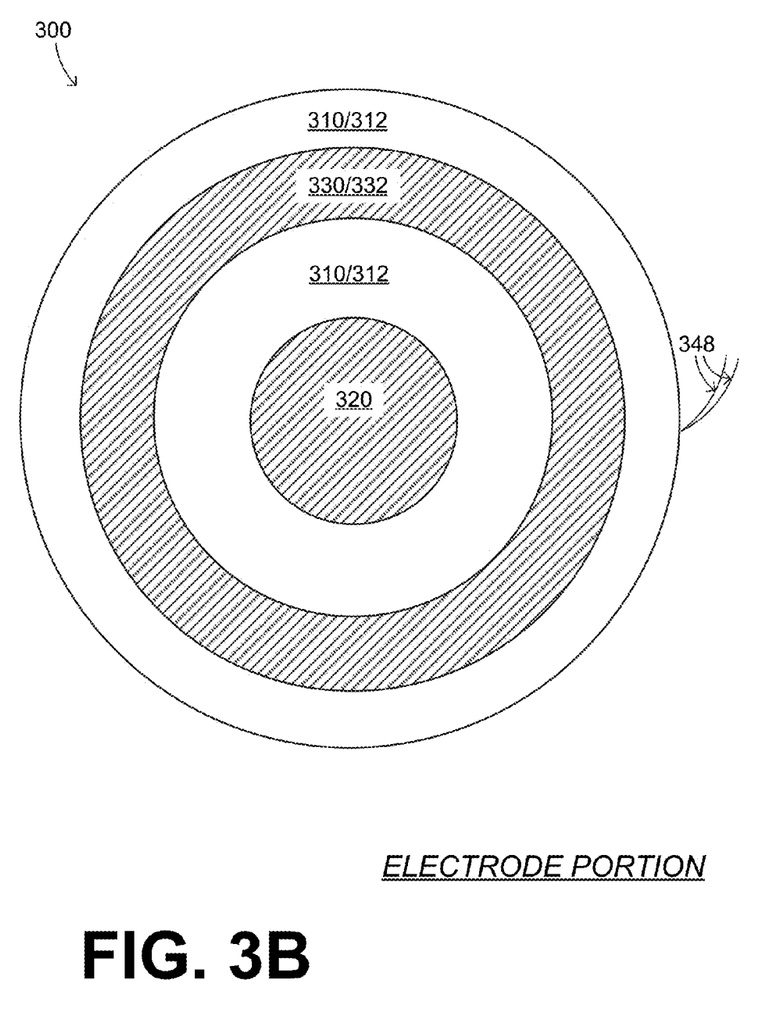
FIG. 3B is a front view of the electrode assembly of FIG. 3A.

Electrode portion 301 additionally includes a guard electrode 330 that has a section 332 a guard stub 334, similarly with FIG. 2. This embodiment is better illustrated by referring to FIG. 3B, which is a front view of the electrode assembly of FIG. 3A. Front side 312 of substrate 310 is an insulator. At the center is the round-shaped plate of sensing electrode 320, which is not designated apart from electrode 320. Section 332 of guard electrode 330 forms a closed loop around the plate of sensing electrode 320, without contacting it. In this example, the closed loop is a ring.

Returning to FIG. 3A, electrode portion 301 further includes a shield 360. Shield 360 is attached to back side 314 of substrate 310, and substantially covers at least a portion of circuit 340 from back side 314. In the shown embodiment, shield 360 covers all of circuit 340 from back side 314. Shield 360 is intended to protect the components and connections on back side 314 from environmental contamination and hazards during the expected use. As such, shield 360 can be made from material that is correspondingly hard, for example plastic, metal etc. It is also possible that shield 360 is a conformal material that is made to be electrically isolated from circuit 340, the electrodes, and the nodes that it may lay across.

In some embodiments, shield 360 includes also a conductive layer, which can be made from material that is conductive like metal or wire mesh. Accordingly shield 360 can be further configured to protect at least partially the portion circuit 340 that it covers, the electrodes, and the nodes from electric fields in the vicinity, the latter of which could cause interference. These fields could be alternating at various frequencies, could carry signals and so on. In some of these embodiments, the shield is coupled to receive a version of the output signal, which can protect against interference even more. Of course, it is understood that the conductive layer of the shield would be so coupled to receive the version of the output signal. The version can be the same version as guard stub 334 receives, or a different version, or just the output signal itself. Alternately, what could be coupled would be a system ground (GND) for EMI suppression. In the shown embodiment, shield 360 has a small opening, and output conductor 350 goes through the opening. In other embodiments, the output conductor may leave the electrode portion from the side, as do power wires 348, without impacting the shield.

Figure 4:
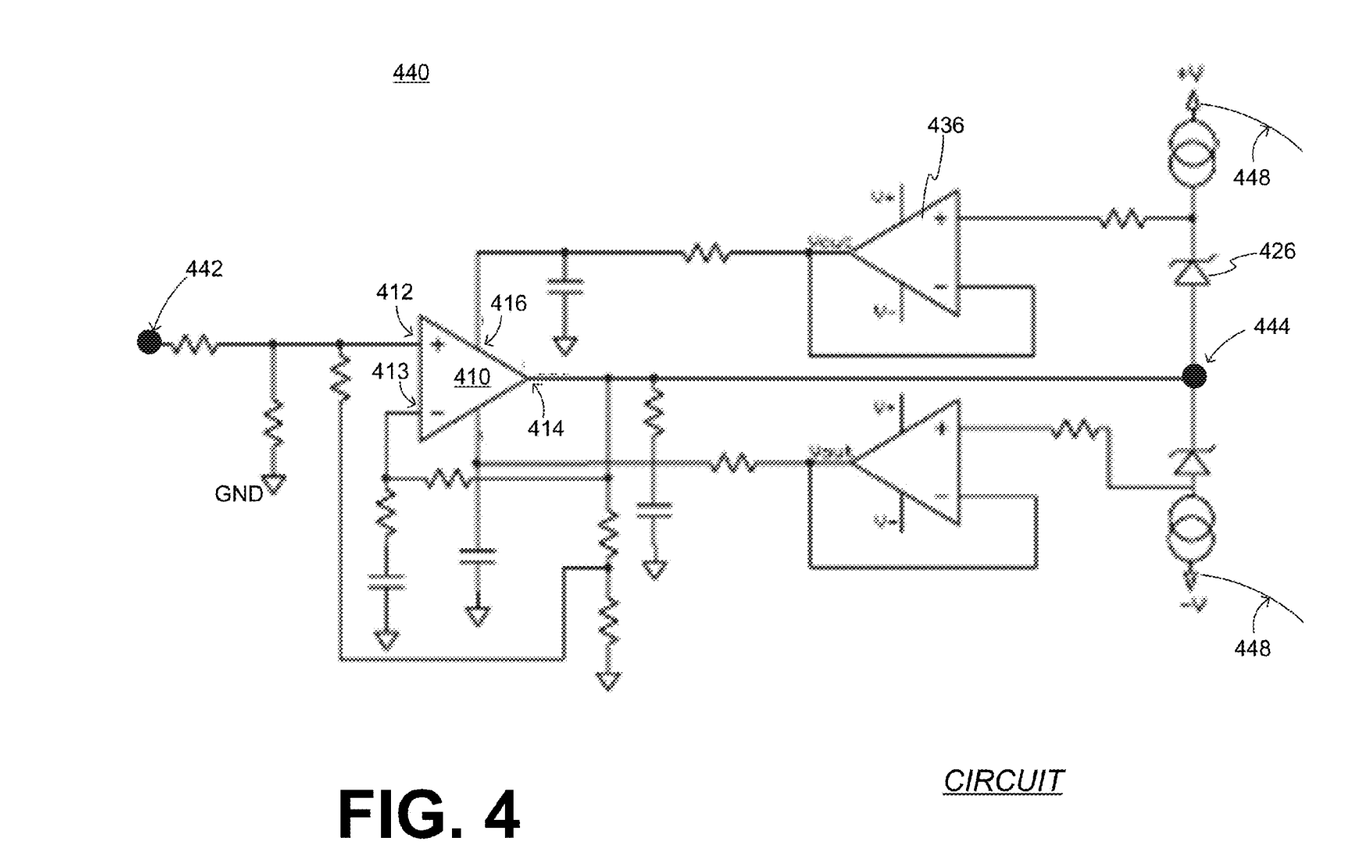
FIG. 4 is a schematic for a circuit of the electrode portion of FIG. 2 or 3A according to an embodiment.

FIG. 4 is a schematic for a circuit 440. Circuit 440 may be used as circuit 240 or 340 in the embodiments of FIG. 2 or 3A, respectively.

Circuit 440 receives power from two power wires 448 that are similar to power wires 148, 248 and 348. It has an input node 442 that can be coupled to the sensing stub and, as such, is similar to input node 242. Circuit 440 also has an output node 444 that can be coupled to the guard stub and also to the output conductor. As such, in this embodiment output node 444 corresponds to both nodes 243, 245, in other words these latter two nodes coincide.

Circuit 440 includes an operational amplifier ("op amp") 410. Op amp 410 has a first input terminal 412, a second input terminal 413, and an output terminal 414. First input terminal 412 is coupled to input node 442, and thus also to the sensing stub. Optionally, second input terminal 413 is coupled to output terminal 414, for example via a resistor.

The output signal is generated at output terminal 414 of op amp 410. Output terminal 414 is coupled to output node 444, and thus also to the guard stub. A filter may be added to the output, as will be described later with reference to FIG. 5.

Op amp 410 operates as a buffer, and helps achieve a transformation of high input impedance to low output impedance for the detected signal. Moreover, op amp 410 includes at least one power terminal 416, through which power is received. Power terminal 416 is also coupled to receive the output signal from output terminal 414. This receiving can be accomplished via a zener diode 426, another op amp 436, or both, for example as shown. Alternately, this receiving can be accomplished via another voltage level translator such as a modified rubber zener, optionally in combination with an op amp, etc. It is important to buffer power terminal 416 from the bootstrapped voltage of the output of op amp 410 to insure no reduction in signal due to finite load impedance. Acting as an impedance buffer, op amp 436 offers the advantages of very high input impedance corresponding low output impedance. Of course, care should be taken to insure closed loop stability. Alternately, op amp 436 can of course be replaced with a simple MOSFET buffer.

Of course, in preferred embodiments, both the positive and the negative power terminals of op amp 410 are treated this way, again as shown. This circuit can also be modified for a single supply operational amplifier in which case the negative supply portion of this circuit is no longer necessary. A bias network can be applied to the patient to insure that the signal received from the patient is nominally at a voltage that is ½ way between the circuit common and the positive supply limit. This could also be valid for an amplifier that is designed to run from ground/common to a negative supply. If there is only one supply, this one supply needs to be "driven".

In embodiments, since the output signal of op amp 410 is rather similar to the detected signal, the effect is that the input signal is applied to the power terminals of the buffer. The effect is that the input signal is actively "bootstrapped" onto the circuit, to effectively reduce the voltage across the input capacitance—in fact bring it close to zero, which can raise the input impedance of op amp 410. Accordingly, circuit 440 implements an interface for a biological transduction electrode with very low input capacitance and very high input resistance. Some embodiments achieve input resistance of the order of $10^{12}$ Ohm, and an input capacitance, which contributes to the input impedance, of less than 10-100 fF (fempto-Farad). The latter permits also the effective input impedance to be very high for the lower frequencies from DC to 250 Hz.

ECG and EEG emissions can be detected by the plate of the sensing electrode. The guard electrode circuitry can be enhanced to provide a current source injection level into the patient's body, for sensing the amplitude modulated signal for other measurements, such as impedance changes due to motion, respiration, EMG analysis, etc.

For the specific task of detecting patient impedance, current may actually be injected into the patient, however, that need not impact the received signal on the inner electrode. This affords the potential of a four electrode impedance system which has been shown to be clearly superior to a two electrode implementation.

Implementations for circuit 440 are now described.

The above shown sample components can be modified. For example, buffer amplifiers 436 can be replaced with discrete transistor components. Moreover, the zener diodes such as zener 426 could be replaced with a modified version of the 'rubber zener' circuitry known by those skilled in the art.

Figure 5:
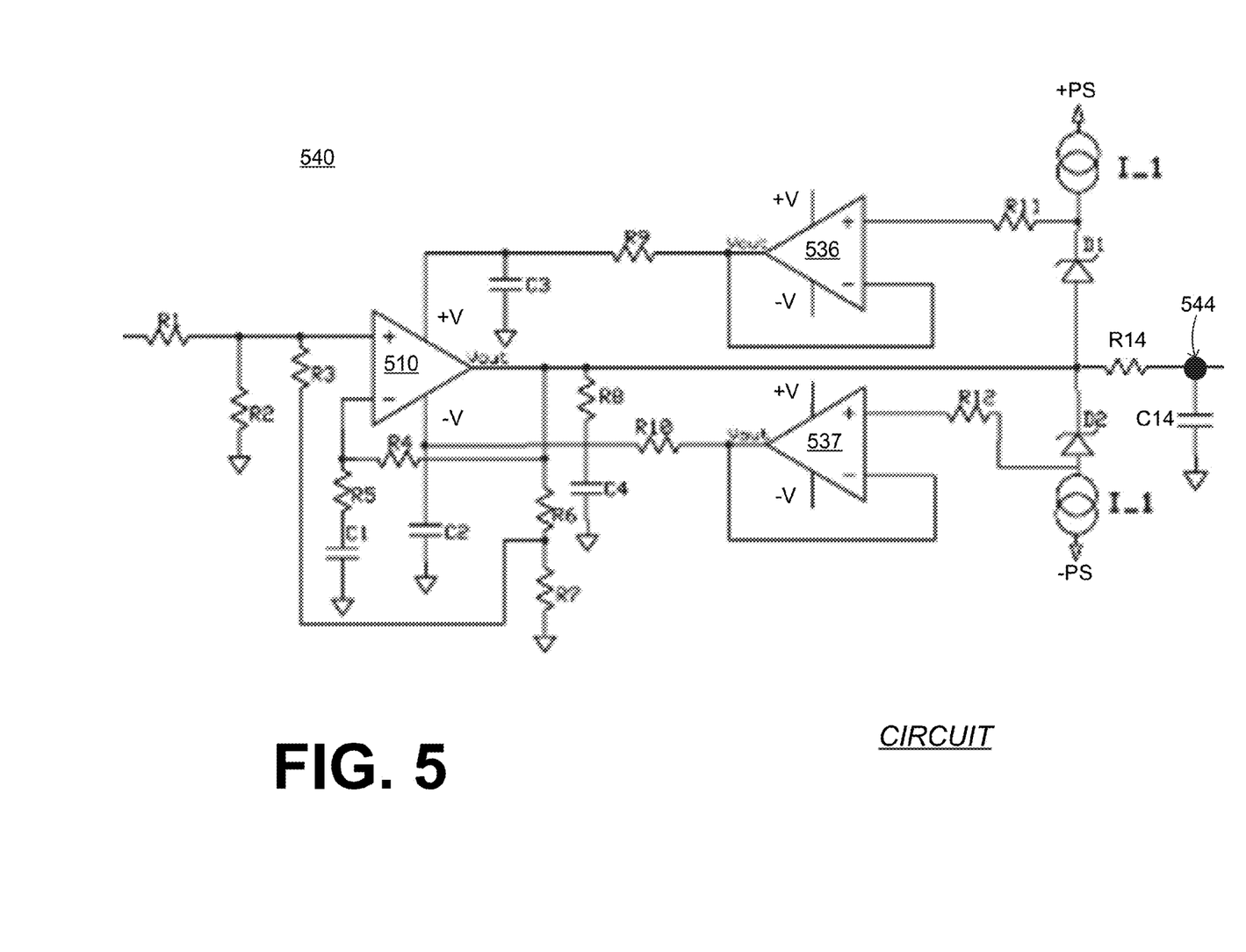
FIG. 5 is a schematic for illustrating sample features of the schematic of FIG. 4.

FIG. 5 is a schematic 540 for illustrating sample features and sample values for schematic 440. The components can be made from off-the-shelf parts. For example, op amps 510, 536, 537 can each be made from an AD8691. Zener diodes D1, D2 can be made from 1N4730A/PS.

Current sources I_1 can be made from transistors in emitter-follower configuration from the power supply nodes +PS/−PS. Power supply nodes +PS/−PS can be +/−10V, +/−15V, or even down to +/−5V. The absolute voltage is not critical, nor the tracking of the positive with the negative.

The combination of R3, R6 and R4 can provide a DC bias current for op amp 510 to be operated at its linear region. It is preferred that the bias current be 1 pA or less for this amplifier to insure proper bootstrap of the bias current to insure very high input impedance.

Resistor R1 is provided for ESD protection, and a good value for it is 2 kOhm. A good value for resistor R2 is 1 Terraohm ($10^{12}$ Ohm).

A good value for resistor R3 is 10 Gigaohm ($10^9$ Ohm)—this impedance is "bootstrapped". Resistor R3 taps into a resistive divider formed by resistors R6 and R7 from the output of op amp 510. Resistors R6 and R7 can have values of 100 Ohm and 10 kOhm respectively. Resistors R4 and R5 can each have a value of 1 kOhm, while capacitor C1 can be 1000 pF.

An optional snubber can be used at the output of op amp 510, made by R8 and C4. Resistor R8 can be 0.1 Ohm to 10 Ohm, and capacitor C4 can be 1000 pF.

Capacitors C3 and C2 are power supply decoupling capacitors for op amp 510, and can be a nominal value of 1 uF. They can receive the power from op amps 536, 537 via resistors R9, R10, which can have values of 10 Ohm.

As mentioned above, an RC filter can be optionally added at the output of op amp 510, and thus output node 544 is not at the same exact place as node 444 was. In this embodiment, the RC filter is implemented by resistor R14, which can be 100 Ohm, and capacitor C14, which can be 100 pF. Resistor R14 can insure stability of the circuit. Capacitor C14 can help with RF immunity.

A person skilled in the art will be able to practice the present invention in view of this description, which is to be taken as a whole. Details have been included to provide a thorough understanding. In other instances, well-known aspects have not been described, in order to not obscure unnecessarily the present invention. Plus, any reference to any prior art in this description is not, and should not be taken as, an acknowledgement or any form of suggestion that this prior art forms parts of the common general knowledge in any country.

This description includes one or more examples, but that does not limit how the invention may be practiced. Indeed, examples or embodiments of the invention may be practiced according to what is described, or yet differently, and also in conjunction with other present or future technologies. Other embodiments include combinations and sub-combinations of features described herein, including for example, embodiments that are equivalent to: providing or applying a feature in a different order than in a described embodiment; extracting an individual feature from one embodiment and inserting such feature into another embodiment; removing one or more features from an embodiment; or both removing a feature from an embodiment and adding a feature extracted from another embodiment, while providing the features incorporated in such combinations and sub-combinations.

In this document, the phrases "constructed to" and/or "configured to" denote one or more actual states of construction and/or configuration that is fundamentally tied to physical characteristics of the element or feature preceding these phrases. This element or feature can be implemented in any number of ways, as will be apparent to a person skilled in the art after reviewing the present disclosure, beyond any examples shown in this example.

The following claims define certain combinations and subcombinations of elements, features and steps or operations, which are regarded as novel and non-obvious. Additional claims for other such combinations and subcombinations may be presented in this or a related document. When used in the claims, the phrases "constructed to" and/or "configured to" reach well beyond merely describing an intended use, since such claims actively recite an actual state of construction and/or configuration based upon described and claimed structure.

What is claimed is:

1. A device configured to detect a physiological signal of a patient, comprising:
    a substrate having a back side and a non-conductive front side that is configured to be brought proximately to the patient;
    a conductive sensing electrode having a plate maintained at the front side of the substrate and a sensing stub that extends from the plate through the substrate to the back side, the plate configured to detect a patient signal when the front side is brought proximately to the patient, the patient signal being defined with respect to a ground;
    a conductive guard electrode having a section maintained at the front side of the substrate and a guard stub that extends from the section through the substrate to the back side, the guard electrode not directly connected to the ground;
    a circuit attached to the back side and coupled to input the detected patient signal from the sensing stub, the circuit further configured to generate an output signal from the inputted detected patient signal, the output signal being a voltage signal, the circuit further coupled so as to couple a version of the output signal to the guard stub so as to electrically bias the guard electrode; and
    an output conductor coupled to receive the output signal from the circuit.

2. The device of claim 1, further comprising:
    an analog to digital converter configured to render a digital value for the output signal carried by the output conductor.

3. The device of claim 1, in which
    the substrate is configured to be fixedly attached to the patient's skin.

4. The device of claim 1, in which
    the plate is attached to the front side.

5. The device of claim 1, in which
    the version of the output signal is the output signal itself.

6. The device of claim 1, in which
    the section of the guard electrode forms a closed loop around the plate of the sensing electrode.

7. The device of claim 1, further comprising:
    a shield on the back side of the substrate and substantially covering at least a portion of the circuit from the back side.

8. The device of claim 7, in which
    the shield is coupled to receive the version of the output signal.

9. The device of claim 7, in which
    the shield is coupled to receive a version of the output signal different from the version of the output signal.

10. The device of claim 7, in which
    the shield is coupled to receive the output signal.

11. The device of claim 7, in which
    the shield has an opening, and
    the output conductor goes through the opening.

12. The device of claim 1, in which
    the circuit includes an operational amplifier having
        a first input terminal coupled to the sensing stub and a second input terminal, and
        an output terminal coupled to the guard stub.

13. The device of claim 12, in which
    the operational amplifier further has at least one power terminal coupled to receive the output signal.

14. The device of claim 13, in which
    the power terminal is coupled to receive the output signal via a zener diode, and/or a voltage level translator, and/or another operational amplifier.

15. A device configured to sense a patient parameter, comprising:
    a substrate having a back side and a non-conductive front side that is configured to be brought proximately to the patient;
    a conductive sensing electrode having a plate attached to the front side of the substrate and a sensing stub that extends from the plate through the substrate to the back side, the plate configured to detect a patient signal when the front side is brought proximately to the patient, the patient signal being defined with respect to a ground;
    a conductive guard electrode having a section attached to the front side of the substrate forming a closed loop around the plate of the sensing electrode, and a guard stub that extends from the section through the substrate to the back side, the guard electrode not directly connected to the ground;
    a circuit attached to the back side and coupled to input the detected patient signal from the sensing stub, the circuit further configured to generate an output signal from the inputted detected patient signal, the output signal being a voltage signal, the circuit further coupled so as to couple a version of the output signal to the guard stub so as to electrically bias the guard electrode;
    a shield on the back side of the substrate and substantially covering at least a portion of the circuit from the back side; and
    an output conductor coupled to receive the output signal from the circuit.

16. The device of claim 15, in which
    the circuit includes an operational amplifier having
        a first input terminal coupled to the sensing stub and a second input terminal,
        an output terminal coupled to the guard stub, and
        at least one power terminal coupled to receive the output signal.

17. The device of claim 16, in which
    the power terminal is coupled to receive the output signal via a zener diode, and/or a voltage level translator, and/or another operational amplifier.

18. A device configured to sense a patient parameter, comprising:
    a substrate having a back side and a non-conductive front side that is configured to be brought proximately to the patient;
    a conductive sensing electrode having a plate maintained at the front side of the substrate and a sensing stub that extends from the plate through the substrate to the back side, the plate configured to detect a patient signal when the front side is brought proximately to the patient, the patient signal being defined with respect to a ground;
    a conductive guard electrode having a section maintained at the front side of the substrate and a guard stub that extends from the section through the substrate to the back side, the guard electrode not directly connected to the ground;
    a circuit attached to the back side and coupled to input the detected patient signal from the sensing stub, the circuit further configured to generate an output signal from the inputted detected patient signal, the output signal being a voltage signal, the circuit further coupled so as to couple a version of the output signal to the guard stub so as to electrically bias the guard electrode;
    a first output conductor coupled to receive the output signal from the circuit;
    a second output conductor; and a multiplexer configured to receive signals from the first and the second output conductors.

19. The device of claim 18, in which the circuit includes an operational amplifier having
a first input terminal coupled to the sensing stub and a second input terminal,
an output terminal coupled to the guard stub, and
at least one power terminal coupled to receive the output signal.

20. The device of claim 19, in which the power terminal is coupled to receive the output signal via a zener diode, and/or a voltage level translator, and/or another operational amplifier.

* * * * *